United States Patent
Ghouri

(10) Patent No.: US 10,643,750 B2
(45) Date of Patent: May 5, 2020

(54) SYSTEM AND METHOD FOR DETERMINING VERACITY OF PATIENT DIAGNOSES WITHIN ONE OR MORE ELECTRONIC HEALTH RECORDS

(71) Applicant: Humana Inc., Louisville, KY (US)

(72) Inventor: Ahmed Ghouri, San Diego, CA (US)

(73) Assignee: Humana Inc., Louisville, KY (US)

( * ) Notice: Subject to any disclaimer, the term of this patent is extended or adjusted under 35 U.S.C. 154(b) by 928 days.

(21) Appl. No.: 14/216,230

(22) Filed: Mar. 17, 2014

(65) Prior Publication Data

US 2016/0357936 A1 Dec. 8, 2016

Related U.S. Application Data

(60) Provisional application No. 61/789,834, filed on Mar. 15, 2013.

(51) Int. Cl.
*G16H 50/70* (2018.01)
*G16H 50/30* (2018.01)
*G16H 10/60* (2018.01)
*G06N 3/08* (2006.01)

(52) U.S. Cl.
CPC .............. *G16H 50/70* (2018.01); *G06N 3/08* (2013.01); *G16H 10/60* (2018.01); *G16H 50/30* (2018.01)

(58) Field of Classification Search
CPC .... G06F 19/3443; G16H 50/70; G16H 10/60; G16H 50/30; G06N 3/08
See application file for complete search history.

(56) References Cited

U.S. PATENT DOCUMENTS

| 2006/0089812 | A1* | 4/2006 | Jacquez | G06F 19/3487 702/23 |
| 2007/0055552 | A1* | 3/2007 | St. Clair | G06F 19/322 705/3 |
| 2012/0290319 | A1* | 11/2012 | Saria | G06Q 50/24 705/3 |

* cited by examiner

*Primary Examiner* — Christopher L Gilligan
(74) *Attorney, Agent, or Firm* — Standley Law Group LLP; Jeffrey Standley; Adam Smith

(57) ABSTRACT

A system and method, using one or more dimensions, that assesses the veracity of a diagnosis presently in a health care record is disclosed. The system assesses the veracity of a diagnosis based on a set of dimension values and a set of weightings. The system also provides a user interface to health care providers/caregivers to review the assessment made by the system and may include a feedback mechanism so that the system may adjust the weighting of the dimensions and improve the assessment of the diagnosis made by the system.

3 Claims, 3 Drawing Sheets

Diabetes – Score = 97/100 (0.97 probability in similar patients)

| Place of Service | No. Related corroborating similar diagnoses from a Valid Entity | Entity making diagnosis | No. of corroborating medications in electronic medical record within past year | No. of corroborating lab values in electronic medical record within past year | No. of corroborating procedures in electronic medical record within past year | Time of most recent potential diagnosis |
|---|---|---|---|---|---|---|
| Doctor's Office | 3 | Physician specialist - Endocrinologist | 4 (e.g., insulin and metformin x two prescriptions each) | 3 (three episodes of glucose > 200 mg/dL) | 2 (pan retinal photocoagulation laser surgery for diabetic eye complications) | 45 days |

Your Evaluation of Reasoned Diagnosis?   <u>True</u>   <u>False</u>

 302

FIGURE 3

SYSTEM AND METHOD FOR DETERMINING VERACITY OF PATIENT DIAGNOSES WITHIN ONE OR MORE ELECTRONIC HEALTH RECORDS

CROSS-REFERENCE TO RELATED APPLICATIONS

This application claims priority to provisional application 61/789,834, filed on Mar. 15, 2013 and is herein incorporated by reference in its entirety.

FIELD

The disclosure relates generally to electronic health records and in particular to a system and method for verifying the accuracy of one or more diagnoses in an electronic health record.

BACKGROUND AND SUMMARY OF THE INVENTION

Electronic health records typically contain codified diagnoses (frequently using standard coding schemes such as ICD9 or SnoMed) such records may also comprise patient clinical problem lists that are required for billing purposes, as well as for maintaining a patient clinical problem list, for subsequent data mining, and for clinical decision support. In a patient data sharing healthcare ecosystem, however, there is co-mingling of diagnoses from multiple providers (who may not know that they may all be treating the same patient), and diagnoses from insurers, which typically include diagnoses amalgamated from suppliers, laboratories, hospitals, nursing homes, imaging facilities, pharmacies, and other entities whose products and services require a diagnosis for payment.

There is therefore a difficulty in determining in a single patient which diagnoses are real and/or currently active when data is shared. These include diagnoses: (1) that are presumptive and created for reimbursement of legitimate services (presumptive diagnosis), (2) diagnoses that are created for services not actually rendered (fraud), (3) diagnoses that do not represent the most severe manifestation of a disease (known as "undercoding") because of lack of caregiver time to encode the most specific condition (e.g., plain "diabetes" vs. "Uncontrolled Type II diabetes with renal manifestations"), (4) diagnoses captured in health records by inadequately trained personnel across the entire spectrum of caregivers (from a generalist physician, to a specialist, to a nurse, to a pharmacist, to a technical assisting with documentation, to self-reported diagnoses by the patient), and finally (5) diagnoses that were once true (e.g., knee sprain, influenza, or routine urinary tract infection from 1 year ago) but would be expected to have time-expired due to the natural history of the illness, and no longer present in a patient's active diagnoses today.

In the case of presumptive diagnosis, by way of example, an imaging facility or laboratory typically records what is known as a 'presumptive' or 'rule-out' diagnosis when it submits a bill for payment. For example, a chest x-ray is commonly associated with a diagnosis of 'pneumonia' when in fact that it is a presumptive diagnosis to include with the image. In many, if not most, instances when a chest x-ray is performed, pneumonia is not found, yet the presumptive diagnosis persists in the patient's medical history.

In electronic health record (EHR) sharing environments, all of these diagnoses can become humanly impossible to sift through in the few minutes a doctor has to treat a new patient, for example.

Therefore, it is desirable to have a system and method in which the veracity of the diagnoses (stored in a patient medical record) can be determined across one or more amalgamated sources of diagnosis data (an example of an amalgamated source of diagnosis date may be a multi-provider health care record or health care records from multiple health care providers) at the current point of care and it is to this end that the disclosure is directed.

Various care data concerning a patient is weighted and processed to provide a likelihood indicator of whether the diagnosis is accurate. The invention can also be used to provide alternative diagnosis for a care provider to consider, ongoing feedback may be used to enhance the reliability of the invention output.

BRIEF DESCRIPTION OF THE DRAWINGS

FIG. 3 illustrates an example of a user interface that may be displayed to a health care provider to review the veracity assessment of an embodiment of the invention.

DETAILED DESCRIPTION OF ONE OR MORE EMBODIMENTS

The system and method may be particularly applicable to a web-based system that delivers diagnosis veracity assessments to one or more health care provider systems over the Internet and it is in this context that the system and method will be described. One skilled in the art will understand that: 1) the system and method may be implemented in various manners that are within the scope of the invention and therefore, that the system and method are not limited to the example web-based system described below; and 2) the system and method may use different dimensions, different coefficients, different formulas, etc than those described below and as such, the system and method are not limited to the examples provided below.

In general, embodiments of the system and method, using one or more dimensions, assesses the veracity of each diagnosis found in a health care record when such a health care record may be an electronic medical record) based on a set of dimension values and a set of weightings, and provides a user interface to health care providers/caregivers to review and verify the assessment made by the system. Embodiments of the system may have a feedback mechanism so that the system may adjust the weighting of the dimensions to improve the assessment of the diagnosis made by the system. The system and method may have a set of dimensions, a weighting of those dimensions, and a veracity determining formula stored/available for each diagnosis (for example, diabetes, cancer, etc.). Since each diagnosis may have unique dimensions/dimension values, unique weighting and/or a unique veracity determining function that may be fine tuned to perform the best possible assessment of the veracity determining formula, weighting for any particular diagnoses may be adjusted over time to fine tune the assessment. In one embodiment, the system and method also may infer a diagnosis for a patient based on the dimensions, the weighting of the dimensions and the function of a particular diagnosis of a particular patient. For example, although a particular patient has not been diagnosed with diabetes, certain tests, lab results, etc. may allow the system to infer that the patient has diabetes. Now, various examples of the embodiments of the system are described in more detail.

Figure 1:
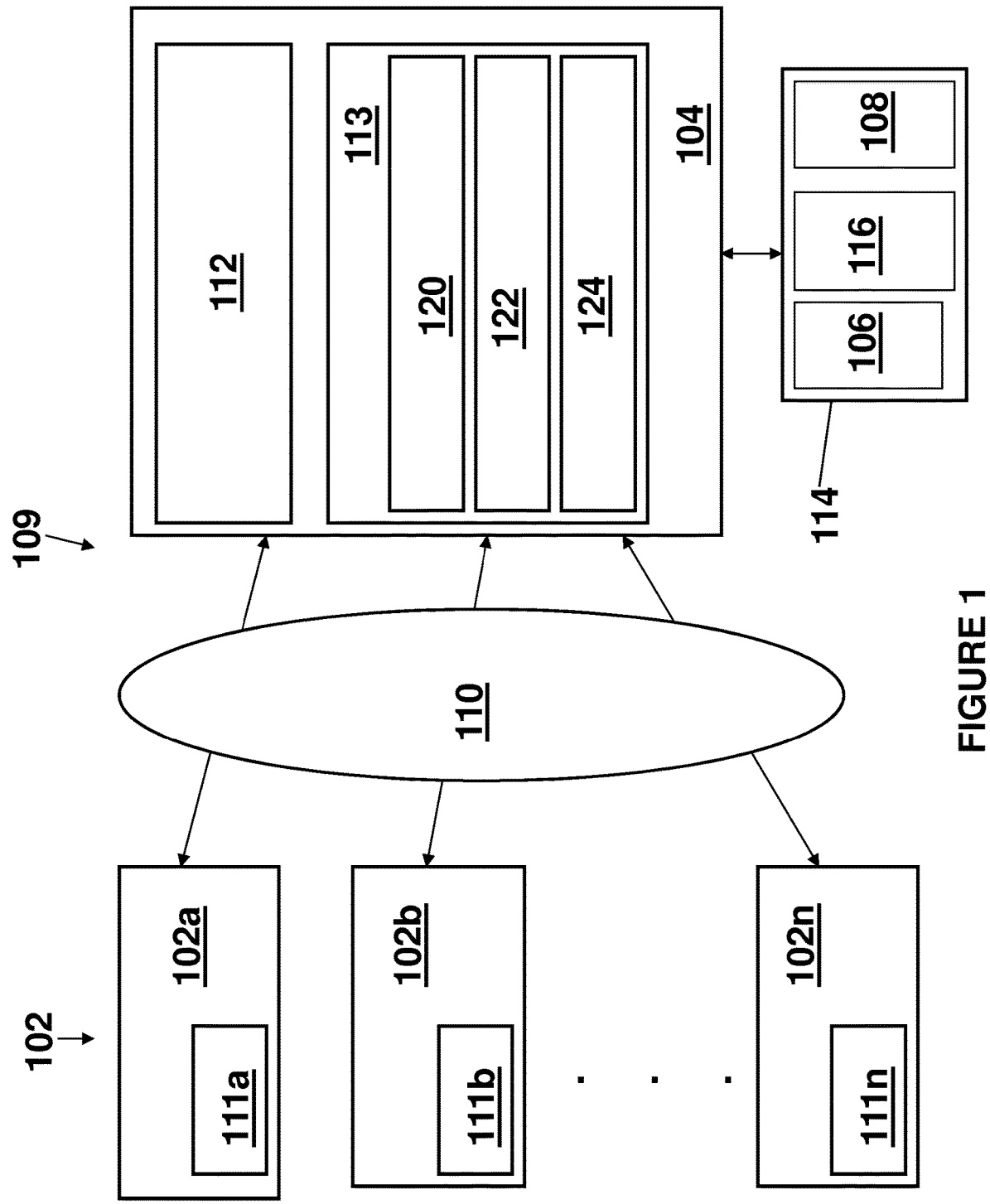
FIG. 1 illustrates an exemplary embodiment of the invention.

FIG. 1 illustrates an example of a web-based implementation of a system 109 and method for diagnosis verification of one or more diagnosis in one or more health care records of a patient that includes one or more health care provider units 102, such as health care provider units 102a, 102b, . . . , 102n, that are capable of establishing a session and communicating with a diagnosis veracity assessment system unit 104 over a link 110. Each health care provider unit 102 may store or have access to a health record/ electronic health record that can be communicated to the system 109 so that the system can analyze multiple health records. The link 110 may be a wired or wireless link, such as the Internet or World Wide Web, cellular network, digital data network, etc., wherein the health care provider unit(s) and the diagnosis veracity assessment unit 104 establish a session and communicate with each other using a communication protocol, such as HTTP or HTTPS. One skilled in the art will realize that other protocols may be used without departing from the spirit of the disclosed invention. Embodiments of the invention are not limited to any particular link or protocol as embodiments may use communications links such as landlines or cellular links, or other network links, such as a local area network, wide area network, etc.

Each health care provider unit 102 may be a computerized device comprised of a computer processor that has sufficient processing power, memory, display capabilities and wireless/wired connectivity circuitry to interact with the diagnosis veracity assessment unit 104. For example, each health care provider unit 102 may be a personal computer, a terminal, a computer server of a health care provider, a multiple provider health care record storage system, a laptop computer, or any number of mobile devices, a pocket PC device, a smartphone (RIM Blackberry, Apple iPhone, etc.), tablet computer, a mobile phone, a mobile email device, etc. Each health care provider unit 102 may also include a typical browser software application 111, such as units 111a, 111b, . . . , 111n, that may be, in an exemplary web-based client/server implementation, a web browser (or a plurality of lines of computer code stored in the health care provider unit and executed by the processing unit of the health care provider unit) that interacts with the diagnosis veracity assessment unit 104 and generates display images with information from the diagnosis veracity assessment unit 104.

The diagnosis veracity assessment unit 104, in one implementation may be implemented as one or more computer servers that may execute one or more software programs. In the web-based example illustrated in FIG. 1, the diagnosis veracity assessment unit 104 may include a software-based web server 112, such as an Apache web server (Apache Software Foundation, www.apache.org) executed by the processing unit(s) of the one or more server computers that establish a communications session with each health care provider unit, generate the web-pages downloaded to each health care provider unit 102, and receives the data/information from each health care provider unit. In embodiments of the invention, the web server 112 may establish multiple simultaneous communication sessions with a plurality of health care provider units 102. Furthermore, health care provider data concerning a patient diagnosis may be obtained from health insurance carrier servers/databases which receive such data for reimbursement to care providers. The diagnosis veracity assessment unit 104 may also be comprised of a diagnosis assessment unit 113, implemented as software instructions executed by the processing unit(s) of the one or more computer servers. The diagnosis veracity assessment units may generate a veracity assessment for each diagnosis in at least one health care record for a patient. In some embodiments of the invention, the veracity assessment units may infer new diagnosis (as described herein) and communicate that assessment to one or more health care provider units.

The system for diagnosis verification 109 may further comprise a data store 114, implemented as one or more databases hosted on one or more database servers in the illustrated implementation. In embodiments of the invention, such a data store may be part of the diagnosis veracity assessment unit 104 or remotely located from the diagnosis veracity assessment unit 104. Such a data store may or may not be owned or controlled by the owner of unit 104. Such a data store 114 may include a plurality of health records 106 for a plurality of patients. Such health records may also be stored in an electronic medical record (EMR) system that is remote from the diagnosis verification system 109. Such a data store may also comprise a dimensions, weighting and rule store 108 that stores the dimensions, weighting of those dimensions, and a function to determine the veracity for a particular diagnosis for a plurality of diagnosis and the assessments for each patient, for each diagnosis (and any diagnosis that may be inferred for a patient).

The plurality of health records 106 may also be one or more health records from one or more health care providers (that may be stored in different locations) for a particular patient so that the system can retrieve all of the health care records for a patient. Access to such a plurality of records may enable the system to analyze a greater range of data when determining the veracity of each diagnosis in the health care records for a patient. In addition, access to records from each care provider to a patient may be provided so that a current health care provider can rapidly determine which diagnosis are correct and which are not accurate. In addition, using the feedback (described later herein), the dimensions, weighting, and functions for any particular diagnosis may be updated and then stored in the data store 108.

The system 109 may also include a user data store 116 that may be used to store various pieces of information about the users of the system. For example, the user data store may have a record associated with each health care provider and its associated users of the system. Such a record may comprise, for example, the preferences for each health care provider and its associated users. Each of the units/portions of the system 109 may be implemented in software, hardware, or a combination of software and hardware, and embodiments of the system should not be considered to be limited to any particular implementation of the system and its units.

Although a typical client/server architecture using web pages is illustrated in FIG. 1, the system can also be implemented as a hosted system, software as a service (SaaS) model, as a health care provider internal system, as a stand-alone system, and other architectures as the system is not necessarily limited to any particular architecture or physical implementation.

The diagnosis assessment unit 113 may comprise a veracity score unit 120 that, using a predetermined set of dimensions, weighting and functions, determine a diagnosis veracity value for the diagnosis of the particular patient. The diagnosis assessment unit may be configured to perform diagnosis veracity value calculations for a plurality of different diagnosis for a plurality of different patients. The diagnosis assessment unit 113 may also have a visualization dashboard generator 122 that generate a diagnosis dashboard for a particular diagnosis that may be returned to the caregiver/health care provider who is treating a patient so that the caregiver/health care provider can view the assessment and confirm the diagnosis assessment of the system. The system may receive such a user confirmation and then "learn" and improve its assessment based on such caregiver/health care provider feedback. To accomplish this, the diagnosis assessment unit 113 may also have a feedback processing system 124 that is closed loop and thus enable machine learning by modifying automatically, or by user or expert input, the dimensions, weighting of the dimensions and/or function used to assess each diagnosis. Such automatic modification may also be applied to the dimensions, weighting of the dimensions and function used to infer a diagnosis by the system. Such feedback enables the system assessments and inferences to be improved in part based on the caregiver or health care provider confirmation of the diagnosis assessments provided by the system over time.

Figure 2:
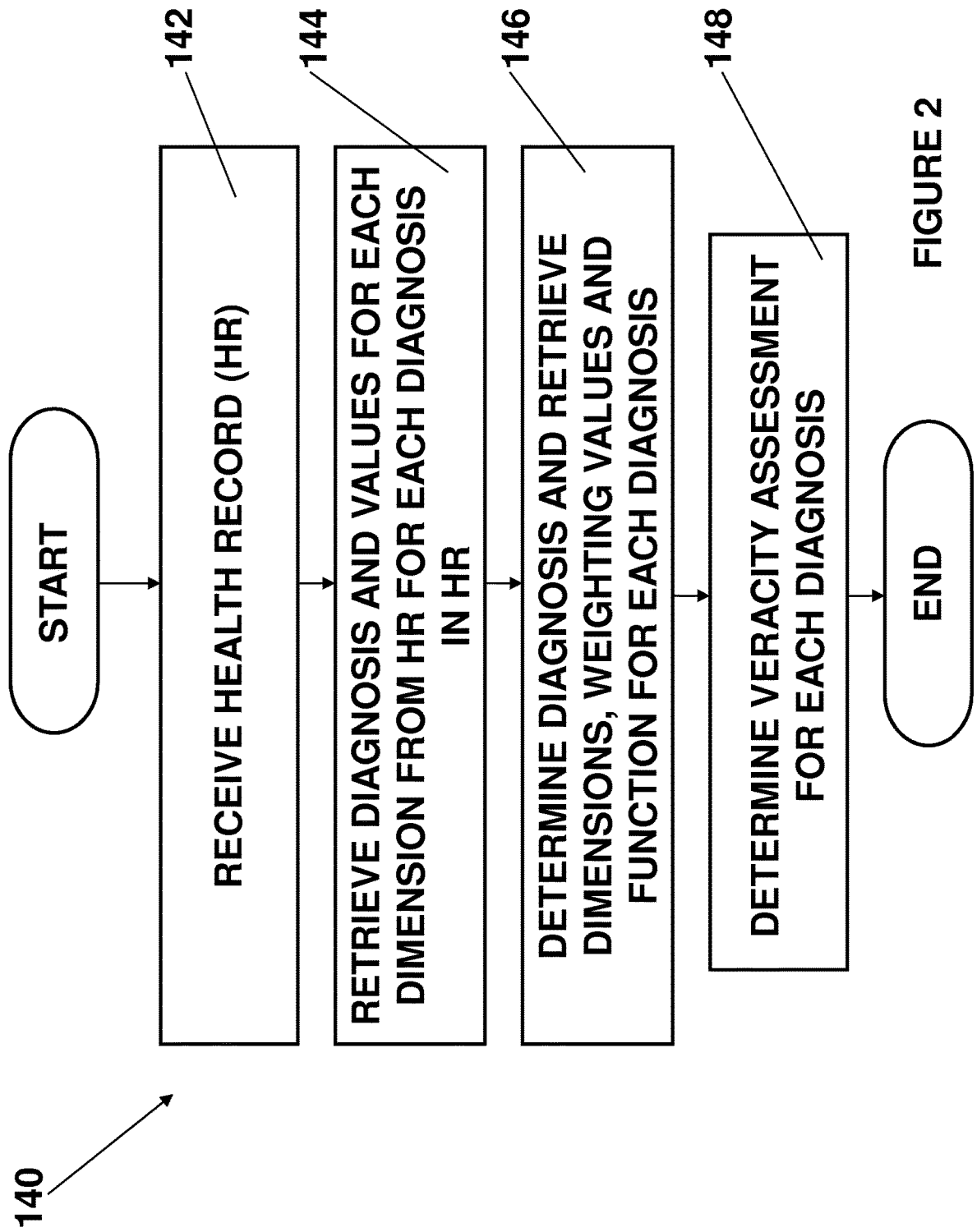
FIG. 2 illustrates a flow chart of an exemplary embodiment of the inventor.

An example of the dimensions, weightings and functions for a particular diagnosis whose veracity can be assessed by the system will now be described. The flow chart of FIG. 2 illustrates an embodiment of a method 140 for determining the veracity of one or more diagnoses for a patient. The following method described is to assess a particular diagnosis for a particular patient at a caregiver site, but the same process steps may be used to assess multiple diagnoses for a patient as well as being used to assess the diagnoses for a plurality of patients. When the method is started (executed by the computerized device of the diagnosis veracity assessment unit 104 in an embodiment), a health care record of a patient (142) that may be in the store of the system or may be located at a remote location/source, is retrieved. In some embodiments, multiple health care records for the patient may be retrieved from one or more health care providers. Once the health care record is received, the diagnosis veracity assessment unit 104 may retrieve a first diagnosis to assess, and may also retrieve the values of the information in the health record (144). The system may then determine the diagnosis and retrieve dimensions, weighting values and function for each diagnosis from the store 108 (146).

Each diagnosis that is assessed by the system may be evaluated using a plurality of dimensions. In one implementation, seven dimensions may be used. The dimensions may be: (1) the type of entity which recorded the diagnosis (e.g., institution, patient, actual caregiver, and if a caregiver the level of training or specialization of the caregiver), (2) the physical location of the diagnosis (e.g., a nursing home, hospital, laboratory, imaging facility), (3) the date of the diagnosis, (4) related similar diagnoses from different entities, (5) medications taken to date that suggest a particular diagnosis, (6) procedures performed to date that suggest a particular diagnosis, and (7) lab values known in the patient's medical history that suggest a particular diagnosis.

The type of entity and physical location dimensions are hierarchical dimensions because there is a hierarchy for the values associate with that dimension. For example, the type of entity dimension may have values that are higher for a physician specialist—Endocrinologist (for a diabetes diagnosis) who is given a higher value (72, for example) than a family practitioner (30 for example), who has a higher value than a nurse (20, for example) who is given a higher value than a patient (10, for example), etc., so that the type of entity value is hierarchical and reflective of the decreasing likelihood (in this example) that each type of entity will make the proper diagnosis. Similarly, the physical location dimension may have values such that a doctor's office is given a higher value (90, for example) than a nursing home (80, for example) which has a higher value than an ambulance (50, for example), which has a higher value than a laboratory (40, for example) that has a higher value than a medical equipment supplier (20, for example), etc., so that the location of diagnosis value is also hierarchical and reflective of the likelihood that each location will have a proper diagnosis made by the person at such a location.

The date of the diagnosis dimension is time value with more recent diagnosis being given a higher value to indicate that a more recent diagnosis is more likely to be accurate. Related similar diagnoses from different entities, medications taken to date that suggest a particular diagnosis, procedures performed to date that suggest a particular diagnosis, and lab values known in the patient's medical history that suggest a particular diagnosis are given numerical values with the number assigned to each type of information being used to assess the veracity of a diagnosis.

Once the dimensions for a diagnosis are determined, the system retrieves the weighting for each dimension for the particular diagnosis. The weighing of each dimension for the particular diagnosis may have a default value, but as was previously described, such default values may be adjusted by the system due to closed loop feedback. The weighting of each dimension may be accomplished by a coefficient. In an exemplary embodiment, the function for a particular diagnosis may have the form of:

Veracity Score for Diagnosis #1=f (a1*Dimension1*b1 Type+Count, a2*Dimension 2 b2*Type+Count, a3*Dimension3*b3 Type+Count, . . . a7*Dimension 7 b7 time)

wherein f is a function and a1, a2, a3, . . . a7 are a weighting coefficient for each corresponding dimension and b1, b2, b3, . . . b7 are each a weighting coefficient to invoke the hierarchy of the particular dimension (if any), and "Count" represents the frequency count of a particular variable. Thus, the final probability (or veracity score) for a particular diagnosis may be a function of the 7 variables and their frequency counts and the time of each event. It is understood that due to iterative feedback over time, the coefficients may be modified, even empirically, such that the likelihood of the diagnosis receiving confirmation as being correct is maximized. Embodiments of the invention may use various different functions and should not be considered as limited to any particular function. For example, the system may use a logistic regression or other weighted, exponential formula (asymptotic, constrains from 0 to 1 for infinite counts and values, etc.).

The system may determine the above described veracity scores for each diagnosis that is part of the health record. The system thus generates a veracity score for each diagnosis (148). The visualization dashboard generator 122 may generate the visualization for each generated diagnosis veracity score with the score, each dimension (and optionally a description of each dimension), and the values associated with each dimension. An example of such a visualization dashboard is shown in FIG. 3. The visualization for a particular diagnosis may be provided to a healthcare provider/caregiver who was involved in the particular diagnosis. The visualization dashboard may display data in a manner that allows the healthcare provider/caregiver to view the diagnosis, the diagnosis veracity score, the dimension and the dimensions values that resulted in the diagnosis veracity score. The visualization dashboard display may also allow the caregiver/heath care provider to evaluate the veracity of the diagnosis score (true or false in the example illustrated in FIG. 3 at 302) which may be communicated back to the diagnosis veracity assessment unit 104 over the link. The feedback system 124 receives the evaluation for each diagnosis from a caregiver/health care provider. Such feedback may then be used by the feedback system 124 to optimize/improve the weighting coefficients for all subsequent patients who have the same diagnosis (e.g., machine learning using multiple patient metadata) so that the diagnosis veracity assessment unit may become more accurate over time as the evaluations are used to adjust the coefficients. For example, the feedback system 124, based on the evaluation, may not modify any of the coefficients and/or modify (increase/lower) some/all of the coefficients in order to improve the accuracy of the veracity score for the particular diagnosis.

The visualization dashboard should provide the caregiver/health care provider with enough information to allow such a caregiver/health care provider to consider the data fully in order to prevent caregiver/health care provider bias just before casting a vote. For example, the caregiver/health care provider may not believe that a patient has diabetes, however, he/she might be confronted with data (which can be from another caregiver) that shows persistent elevated blood sugar, ophthalmic complications specific to diabetes, and/or repetitive use of medications that treat diabetes and resulted in a therapeutic response, such as a lowering of blood sugar values. When provided with such data, the caregiver may vote for the correctness of the diagnoses, when without such information, he or she otherwise may not have done so. By way of example, a table similar to what is shown in the visualization dashboard illustrated in FIG. 3 may be constructed for each potential diagnosis.

In addition to the generating of the diagnosis veracity score as described above, the system may also identify previously unidentified diagnosis in a health record. In particular, based on the same dimensions, weighting and formulas described above, the system can infer certain diagnoses of a patient's condition. For example, the system may retrieve data from the patient's health care record that indicates a persistent elevated blood sugar, ophthalmic complications specific to diabetes, and/or repetitive use of medications that treat diabetes and resulted in a therapeutic response, such as a lowering of blood sugar values. These values of the dimensions can be used by the system to infer that the patient has diabetes even though there is not a diabetes diagnosis in the patient's health record. For example, if the veracity score for a particular previously unreported diagnosis is about a predetermined threshold (such as 90%), then the diagnosis becomes an inferred diagnosis. Conversely, patient data trending in the opposite direction would indicate that a diabetes diagnoses is incorrect. While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A system for optimizing a veracity score for a particular diagnosis of a plurality of diagnoses associated with a patient, the system comprising:
   a plurality of healthcare provider units, each of which comprise a display;
   a store that stores, for each of the plurality of diagnoses associated with the patient, a set of weighting coefficients, a set of dimensions, and a function;
   a computer server comprising executable software instructions, which when executed configure the computer server to:
   retrieve a health record of a patient from at least one of the plurality of healthcare provider units and generate a diagnosis veracity score for each of the plurality of diagnoses contained in the health record of the patient, wherein the plurality of diagnoses comprises the particular diagnosis;
   for the particular diagnosis:
      retrieve from the store a set of values, wherein each of the set of values is associated with one of the set of dimensions for the particular diagnosis from the health record, wherein each of said set of values is selected to reflect the likelihood that the associated dimension in the set of dimensions represents a reliable indicator of the particular diagnosis, said set of dimensions comprising: the type of entity which recorded the diagnosis, the date of the diagnosis, medications taken to date that suggest the particular diagnosis, and lab values that suggest the particular diagnosis;
      retrieve from the store the set of weighting coefficients for the particular diagnosis wherein each dimension has a weighting coefficient associated with it, and wherein each of the weighting coefficients is selected to reflect the likelihood that the associated dimension of the set of dimensions is a reliable indicator of the particular diagnosis relative to other dimensions in the set of dimensions;
      retrieve from the store the function for the particular diagnosis, wherein said function comprises said weighting coefficients and dimensions;
      determine automatically a veracity score for the particular diagnosis by multiplying each of the retrieved weighting coefficients with the associated retrieved dimension to arrive at a value and applying each of the values to the retrieved function, wherein said veracity score is a numerical percentage value;
      generate, for the particular diagnosis, a visualization dashboard for display on the display of at least one of the healthcare provider units, said visualization dashboard comprising:
         a table comprising:
            a set of dimensions for the particular diagnosis; and
            a set of values for the set of dimensions for the particular diagnosis;
            wherein each of the set of dimensions for the particular diagnosis are associated within the table with one of the set of values;
         the particular diagnosis veracity score; and
         a caregiver evaluation tool for providing feedback regarding the particular diagnosis veracity score, wherein said caregiver evaluation tool comprises a prompt for receiving a user selection of true or false; and
      receive a caregiver evaluation comprising the user selection of true or false by way of the caregiver evaluation tool and automatically optimize the set of weighting coefficients for the particular diagnosis by modifying one or more of the set of weighting coefficients which are subsequently stored in the store based upon the received caregiver evaluation to improve the accuracy of the veracity score;

wherein the function for the particular diagnosis is a logistic regression, a weighted function, or an exponential function.

2. The system of claim 1, wherein the computer server executes software instructions to infer a new diagnosis not contained in the health record based on the veracity score of the new diagnosis.

3. The system of claim 1, wherein the computer server executes software instructions to determine the veracity of each diagnosis of the patient contained in all health records for a patient.

\* \* \* \* \*